United States Patent [19]

Tritt

[11] Patent Number: 4,681,105
[45] Date of Patent: Jul. 21, 1987

[54] MICROSURGICAL TOOL

[75] Inventor: Eugen Tritt, Jestetten, Fed. Rep. of Germany

[73] Assignee: S+T Marketing AG, Neuhausen a. Rheinfall, Switzerland

[21] Appl. No.: 486,219

[22] Filed: Apr. 18, 1983

[30] Foreign Application Priority Data

Apr. 19, 1982 [DE] Fed. Rep. of Germany ....... 3214318

[51] Int. Cl.[4] .............................................. A61B 17/39
[52] U.S. Cl. ................................ 128/303.17; 219/90; 219/234
[58] Field of Search ...................... 128/303.13, 303.14, 128/303.17, 354, 303.1; 219/90, 234

[56] References Cited

U.S. PATENT DOCUMENTS

| 1,071,978 | 9/1913 | White | 128/354 |
|---|---|---|---|
| 2,429,039 | 10/1947 | Warner | 219/90 X |
| 2,882,386 | 4/1959 | Hermanny | 219/90 |
| 3,100,489 | 8/1963 | Bagley | 128/354 X |
| 3,354,478 | 11/1967 | Allen | 219/90 X |
| 3,768,482 | 10/1973 | Shaw | 128/303.14 X |
| 3,911,241 | 10/1975 | Jarrard | 128/303.17 |
| 3,980,861 | 9/1976 | Fukunaga | 128/303.1 |
| 4,228,800 | 10/1980 | Degler, Jr. et al. | 128/303.14 |

FOREIGN PATENT DOCUMENTS

| 2841492 | 4/1980 | Fed. Rep. of Germany | 128/303.17 |
|---|---|---|---|
| 3012849 | 10/1981 | Fed. Rep. of Germany | 128/303.13 |

Primary Examiner—Lee S. Cohen
Attorney, Agent, or Firm—Lalos & Keegan

[57] ABSTRACT

A microsurgical pincette consists of two metallic arm members and a metallic connection member, rigidly fixing the two arm members one to each other at an end region of the arm members. To ensure an electric insulation between the two arm members, a part of their length, including said end region, is provided with an oxide protection coating, preferably consisting of aluminium oxide, applied by plasma coating technique.

8 Claims, 2 Drawing Figures

MICROSURGICAL TOOL

BACKGROUND OF THE INVENTION

1. Field of the Invention

The present invention refers to a microsurgical tool, in particular to a pincette or a pair of tweezers useful in microsurgical work. Such tools may be used in microsurgery, amongst else, as so-called coagulation pincettes. For this purpose, they include, usually at the end region where the two pincette arms are fixed together, electrical terminals to be connected to a power supply, usually a high frequency power oscillator. Thereby such pincettes may be used to block small blood vessels by clamping them between the two arms of the pincette and applying the high frequency power thereto. Of course, it is of paramount importance that the two arms of the pincette be electrically isolated one from each other to avoid an unintended shorting of the power supply or to prevent a leak current to flow through the pincette.

2. Prior Art

Known coagulation pincettes of the kind described above comprise a plastic member to fix the two arms of the pincette and to simultaneously isolate them from each other. The plastic member is arranged at an end region of the pincette arms and provides a rigid mechanical fixing and an electrical insulation between the arms. However, the plastic material has only a very limited resistance to heat, and consequently, the temperature at sterilisation of such pincettes, which is absolutely necessary after having used it, must be comparatively low to avoid a destruction of the plastic material. Nevertheless, the useful life and the mechanical strength of the plastic fixing member is decreased after every sterilisation and moreover, the electrical insulating properties become worse.

OBJECTS OF THE INVENTION

It is an object of the present invention to provide a surgical tool, in particular a pincette, which may be used as a coagulation pincette having an increased useful life, which can be sterilised at very high temperatures without the danger of any damage to any of its components. A further object of the invention is to provide a tool of the kind described above which has excellent electrical insulating characteristics, which are not degraded by frequent subjecting the tool to very high temperatures. A still further object of the invention is to provide a tool of the kind described above which can be easily manufactured at comparatively low costs.

SUMMARY OF THE INVENTION

The invention provides a surgical tool comprising a first and a second arm member and a metallic connection member adapted to fix said first arm member to said second arm member at an end region of said first and second arm members, thereby providing a rigid mechanical connection between said two arm members. To further ensure a good and durable electrical insulation between said two arm members, at least one of said arm members is provided with a covering layer extending at least over said end region and consisting of an oxide protection coating applied to the surface of said at least one arm member by plasma coating technique. Thereby, said metallic connection member is in contact with at least one of said end regions of the arm member via at least said oxide protection coating.

In most cases it may be desirable to cover both of said arm members with said protective oxide coating and to apply said coating along the major parts of the length of the arms, even if it is basically necessary to cover only the end region of the arms, which is in contact with the connection member, with the protective oxide coating. To realize a further advantage, i.e. a better gripping ability and a higher resistance against wear, it may be desirable to provide approximately 4/5th of the length of both arm members with the protective coating.

It has been proven advantageous to use aluminium oxide as the aforementioned protective coating, which may easily be applied by plasma coating technique. This is a well known, reliable coating technique to create layers consisting of metal oxides on metal substrates. This technique is used, e.g., in the aviation industry to provide metal parts with a hard coating with high resistance against wear.

BRIEF DESCRIPTION OF THE DRAWINGS

In the following, there will be described an embodiment of the tool according to the present invention, with reference to the accompanying drawings, in which.

DESCRIPTION OF A PREFERRED EMBODIMENT

Figure 1:
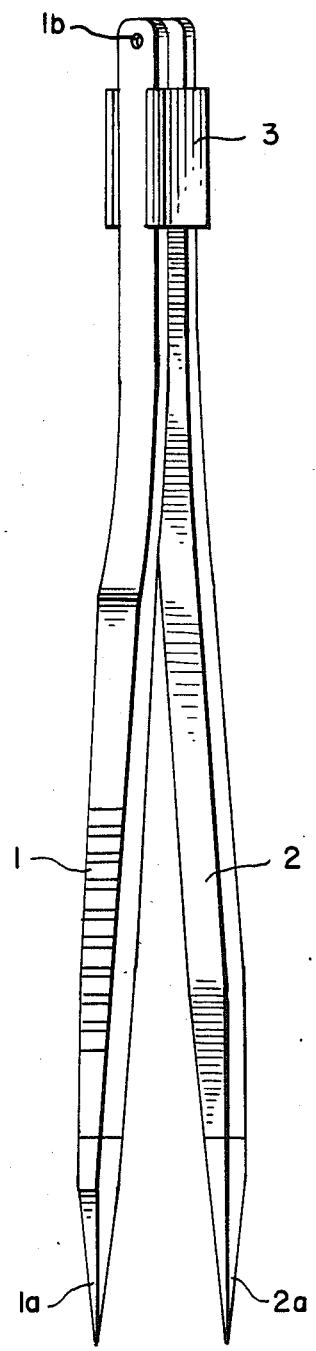
FIG. 1 shows a perspective, schematical view of a coagulation pincette.
Figure 2:
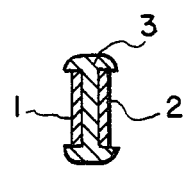
FIG. 2 shows a cross section through the pincette of FIG. 1 at the metallic connection member fixing the two arms of the pincette to each other.

The pincette shown in FIG. 1 of the drawings comprises two resilient arm members 1 and 2, made of stainless steel and having the usual shape. The two arms have each a tip region 1a and 2a, respectively, and comprise an oxide protection coating, beginning after the tip regions 1a and 2a and extending along the major part of their length up to an end region of each pincette arm member. This oxide protection coating consists of aluminium oxide applied by plasma coating technique and is shown in Fig. 1 by cross-hatching. In plasma coating technique, molten metal oxide particles, especially aluminium oxide particles, are thrown to the surface of the metallic arms 1 and 2.

The back end regions of the arm members 1 and 2 are fixed in a connection member 3, which is made of metal, preferably of stainless steel. As the connection member contacts but the electrically non-conductive oxide protection coating on the surface of the arm members 1 and 2, the arm members 1 and 2 are electrically isolated one from each other and also against the metallic connection member 3. Therefore, an electric voltage can be fed to the two arm members 1 and 2 by connecting a suitable power supply (e.g. a high frequency power oscillator) which is not shown in the drawings, to the two arm members 1 and 2. Of course, the arm members 1 and 2 have to be provided with suitable connection terminals. Such a terminal is schematically shown by a bore 1b in the end region of the arm member 1, the bore penetrating the oxide protection coating and offering access to the metallic material of the arm member 1.

If a suitable frequency power supply is connected to the arm members 1 and 2, the tool shown in FIG. 1 may be used as a coagulation pincette in microsurgery to block small blood vessels. However, such tool may be used in a variety of other applications, e.g. the in electronic industry.

Compared with known tools of the kind described above, which generally make use of a plastic insulation member, often also used as a connection member to fix the two arm members one to each other, a tool according to the invention including oxide protection coating on the two arms 1 and 2 and a metallic connection member 3 used to fix the two arm members mechanically, offers the following advantages:

improved resistance against mechanical stress;
improved chemical resistance, particularly against acids;
improved resistance against high temperatures, thereby offering the possibility for high temperature sterilisation in a steam autoclave.

The oxide protective coating will not be damaged by temperatures up to 2000 degree celsius and maintains its excellent electrical insulation characteristics even after prolonged exposure to very high temperatures.

As can be seen from the drawing, the arm members 1 and 2 of the preferred embodiment of the coagulation pincette are nearly completely covered by the oxide protection coating, except the tip regions 1a and 2a and the terminal bore 1b, i.e. along approximately 4/5th of their length. However, as it is mainly important to provide a good electrical insulation between the arm members 1 and 2 and between the connection member 3 and the arm members, it would be sufficient to cover only those regions of the arm members 1 and 2 with said protective coating which are in contact with the metallic connection member 3. Furthermore, there exists the possibility to cover only one of the two arm members, either 1 or 2, with said protective coating, as this would be sufficient to electrically isolate the two arm members from each other.

In order to prevent the oxide protection coating from being damaged during the installation and fixing of the connection member 3, it may be advantageous to provide a pressure equalization layer between the member 3 and the protective coating on the arm members 1 and 2. Such additional layer, however, is not shown in the drawings. Thereby, the pressure exerted onto the macroscopically uneven surface of the protective coating is equalized and any danger of locally damaging the coating is avoided, which could lead to a degrading of the insulating properties. The equalization layer does not need to be electrically insulating, but should have good characteristics in view of thermal resistance and aging.

What I claim is:

1. A microsurgical tool comprising:
a first metallic arm member having a first end region and a second metallic arm member having a second end region,
a metallic connection member fixing together said first arm member and said second arm member at the end regions of said first and second arm members for providing a mechanically rigid connection between said two arm members,
electrically insulating means intermediate said connection member and at least one of said arm members for electrically insulating the metallic arm members from each other,
said insulating means including at least one of said arm members being provided with an insulating covering layer circumscribing and extending at least over one of said end regions and consisting of an oxide protection coating applied to the surface of said at least one arm member by plasma coating,
said metallic connection member being in contact with at least one of said end regions of said arm members via at least said oxide protection coating, and
a pressure equalization layer between the oxide protection coating and said metallic connection member.

2. A microsurgical tool according to claim 1, wherein both of said first and said second arm members are covered by said oxide protection coating along the major part of their length.

3. A microsurgical tool according to claim 2, wherein said oxide protection coating is applied along 4/5th of the length of said first and said second arm members.

4. A microsurgical tool according to anyone of the claims 1 to 3, wherein said oxide protection coating at least partially consists of aluminium oxide.

5. A microsurgical tool according to any one of the claims 1 to 3, wherein said oxide protection coating consists essentially of aluminum oxide.

6. A microsurgical tool comprising:
(a) a first metallic arm member having a first end region and a second metallic arm member having a second end region;
(b) a metallic connection member to which said first arm member and said second arm member are fixed at the end regions of said first and second arm members, electrically insulating means fixed intermediate said connection member and said arm members for providing a mechanically rigid connection therebetween;
(c) each of said arm members being provided with an insulating covering layer covering said arms and extending at least over said end regions and covering at least about one half of each of said arms, said layer consisting of an oxide protection coating applied to the surface of said arms by plasma coating technique, and said insulating means fixed intermediate said connection member and said arm members including said insulating covering layer;
(d) said metallic connection member being in contact with said regions of said arm members via said oxide protection coating.

7. The microsurgical tool according to claim 6 wherein said covering layer extends over an area of about four-fifths of each of said arms leaving ends remote from said end region uncovered for electrical contact.

8. The microsurgical tool according to claim 6 wherein each of said end regions includes a bore penetrating said end region to provide terminals for electrical connections to an electrical source.

* * * * *